United States Patent
Ponzi

[11] Patent Number: 5,938,603
[45] Date of Patent: Aug. 17, 1999

[54] STEERABLE CATHETER WITH ELECTROMAGNETIC SENSOR

[75] Inventor: Dean M. Ponzi, Glendora, Calif.

[73] Assignee: Cordis Webster, Inc., Baldwin Park, Calif.

[21] Appl. No.: 08/982,064

[22] Filed: Dec. 1, 1997

[51] Int. Cl.[6] .................................................. A61B 5/05
[52] U.S. Cl. ........................................ 600/424; 604/280
[58] Field of Search ................................ 600/424, 407; 604/95, 280; 607/122, 115; 128/899

[56] References Cited

U.S. PATENT DOCUMENTS

| | | | |
|---|---|---|---|
| 5,242,441 | 9/1993 | Avitall | 606/41 |
| 5,318,525 | 6/1994 | West et al. | 604/95 |
| 5,391,199 | 2/1995 | Ben-Haim | 607/122 |
| 5,431,168 | 7/1995 | Webster | 128/658 |
| 5,443,489 | 8/1995 | Ben-Haim | 607/115 |
| 5,454,370 | 10/1995 | Avitall | 128/642 |
| 5,462,544 | 10/1995 | Saksena et al. | 606/15 |
| 5,489,270 | 2/1996 | Van Erp | 604/95 |
| 5,546,951 | 8/1996 | Ben-Him | 128/702 |
| 5,555,883 | 9/1996 | Avital | 128/642 |
| 5,715,832 | 2/1998 | Koblish et al. | 128/754 |
| 5,730,704 | 3/1998 | Avitall | 600/374 |
| 5,755,760 | 5/1998 | Maguire et al. | 607/122 |

*Primary Examiner*—Marvin M. Lateef
*Assistant Examiner*—Elenki Mantis Mercader
*Attorney, Agent, or Firm*—Christie, Parker & Hale, LLP

[57] ABSTRACT

A steerable electromagnetic catheter comprises a catheter body, tip section, and control handle. The catheter body has proximal and distal ends and at least one lumen extending therethrough. The control handle is fixedly attached to the proximal end of the catheter body. The tip section comprises tubing having proximal and distal ends and at least one lumen extending therethrough. The proximal end of the tip section is fixedly attached to the distal end of the catheter body. A tip electrode is mounted at the distal end of the tip section and has at least one blind hole extending from its proximal end. The blind hole is in communication with at least one lumen in the tip section. An electromagnetic sensor is mounted in the tip section. The catheter further comprises a means for deflecting the tip section.

31 Claims, 5 Drawing Sheets

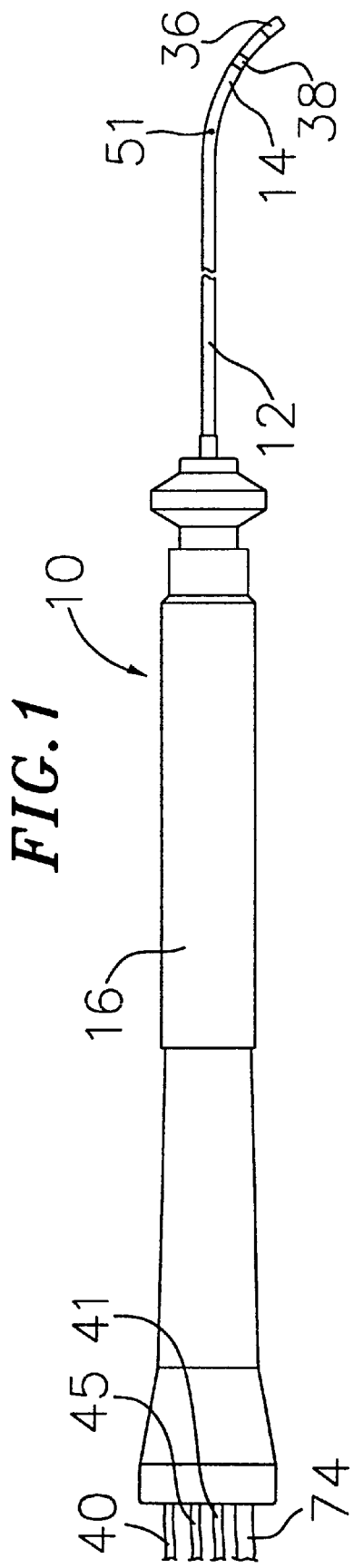

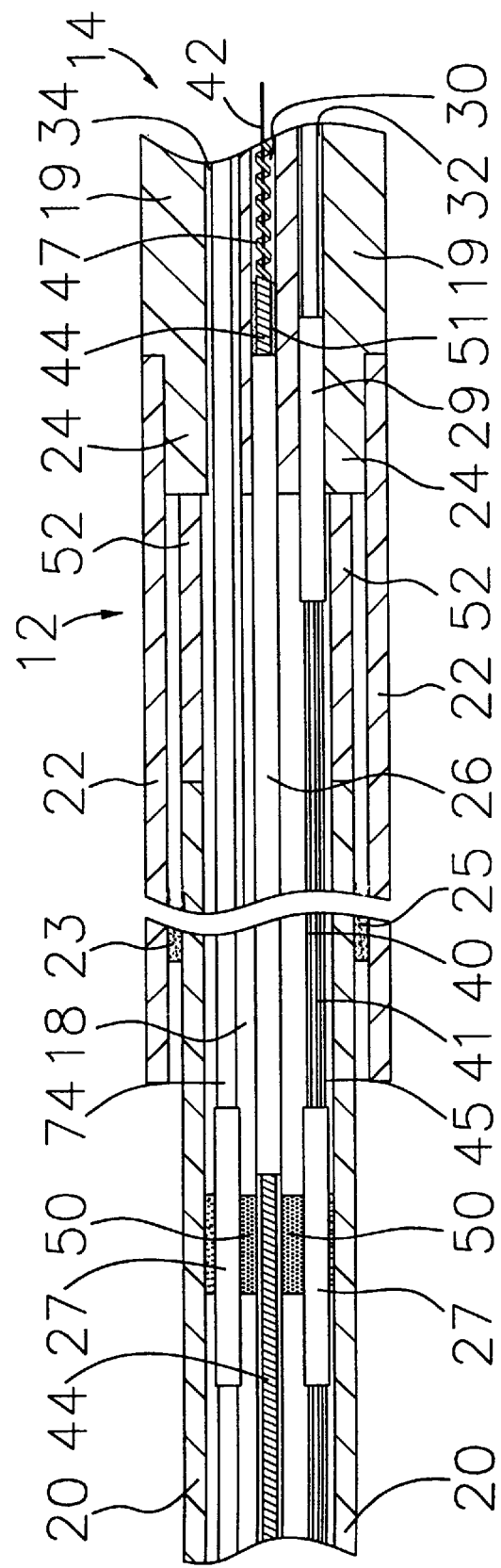

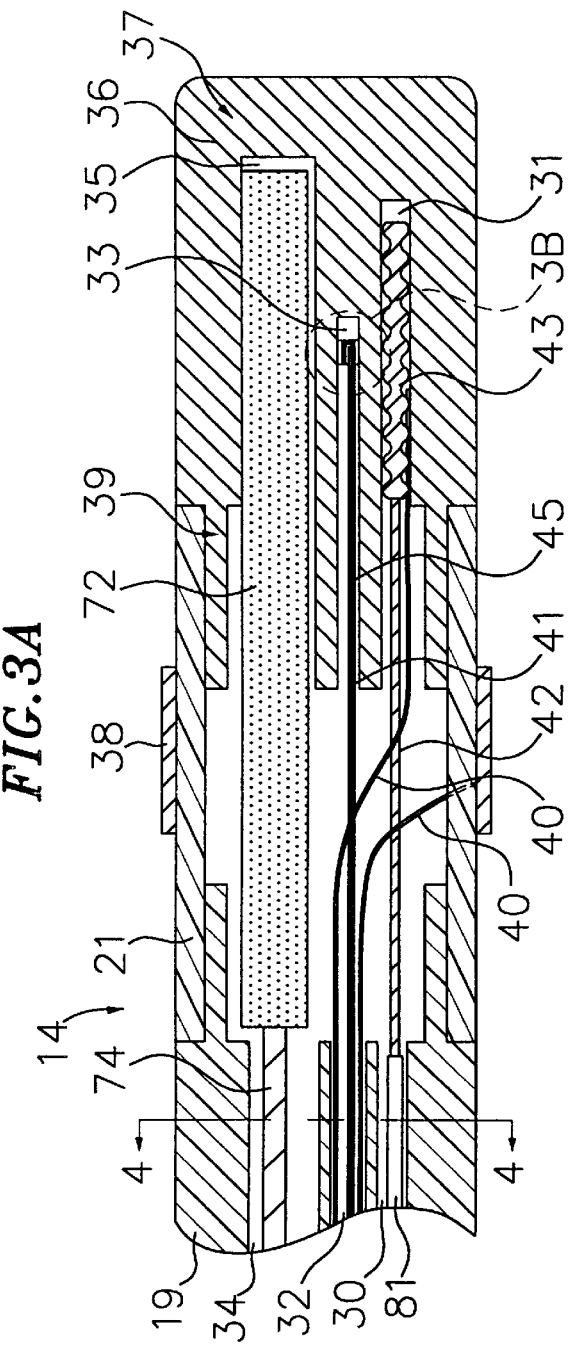
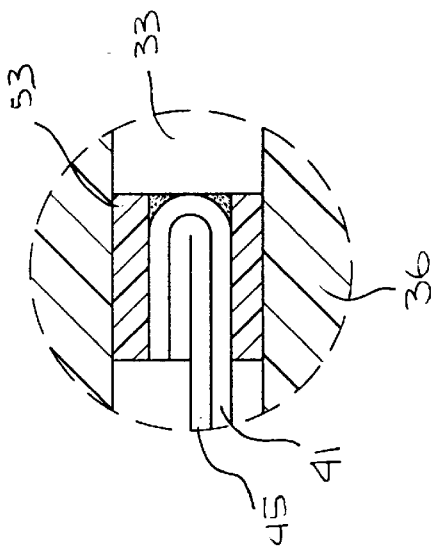

STEERABLE CATHETER WITH ELECTROMAGNETIC SENSOR

FIELD OF THE INVENTION

The present invention relates to a steerable catheter containing an electromagnetic sensor.

BACKGROUND OF THE INVENTION

Electrode catheters have been in common use in medical practice for many years. They are used to stimulate and map electrical activity in the heart and to ablate sites of aberrant electrical activity.

In use, an electrode catheter is inserted into a major vein or artery, e.g., femoral artery, and then guided into the chamber of the heart which is of concern. Within the heart, the ability to control the exact position and orientation of the catheter tip is critical and largely determines how useful the catheter tip is.

Steerable tip electrode catheters are well known. Such a catheter generally has a control handle at its proximal end for controlling deflection of the tip in one or more directions. For example, a particularly useful steerable tip catheter is disclosed in U.S. Pat. Nos. 4,960,134 and Re. 34,502 to Webster, the disclosures of which are hereby incorporated by reference. This catheter comprises a puller wire which extends on-axis through an elongated reinforced catheter body and then off-axis in a deflectable tip portion. In this arrangement, longitudinal movement of the puller wire relative to the catheter body results in deflection of the catheter tip portion. Other examples of steerable catheters can be found in U.S. Pat. No. 5,431,168 to Webster and U.S. patent application Ser. No. 08/924,611 to Webster entitled "Omni-Directional Steerable Catheter," the disclosures of which are hereby incorporated by reference.

U.S. Pat. No. 5,391,199 to Ben-Haim, discloses a non-deflectable electrode catheter with an imaging system for the treatment of cardiac arrhythmias, the disclosure of which is hereby incorporated by reference. The electrode catheter comprises an electromagnetic sensor adjacent the tip electrode at the distal tip of the catheter. The system allows an operator to create a three dimensional image of the heart chamber and to monitor the position of the sensor, and hence the tip electrode within that three dimensional image of the heart chamber. The electromagnetic sensor disclosed is generally cylindrical and has a relatively large outside diameter of about 6 to 7 French (1 French=approximately 0.013 inch). This large diameter creates numerous difficulties in designing a small diameter, e.g., 8 French, steerable catheter incorporating an electromagnetic sensor. Further, the sensor must be completely insulated from the electrodes and electrode lead wires to perform properly.

In addition, the presence of the electromagnetic sensor along with the tip electrode imparts rigidity to the distal end of the catheter tip section. These characteristics create further difficulties in designing a small diameter, steerable catheter comprising an electromagnetic sensor.

SUMMARY OF THE INVENTION

The present invention is directed to a steerable electromagnetic catheter useful for mapping three-dimensional images of the heart and locating a catheter tip within the heart. The catheter comprises a catheter body, a tip section, and a control handle. The catheter body has proximal and distal ends and at least one lumen, and preferably only one lumen, extending therethrough.

The tip section comprises a tubing having proximal and distal ends with the proximal end of the tip section fixedly attached to the distal end of the catheter body. The tip section has at least one, and preferably three, lumens extending through its length. The tip section preferably has a diameter of 7 French.

A tip electrode is mounted at the distal end of the tip section. The tip electrode has at least one blind hole, and preferably three blind holes, extending from its proximal end. Each blind hole is in communication with at least one lumen in the tip section.

An electromagnetic sensor for receiving locating information within the heart is mounted in the tip section. The distal end of the sensor is mounted within a blind hole in the tip electrode and the proximal end of the sensor extends into the tubing of the tip section. Preferably a generally rigid tubular housing is provided for housing the sensor. The distal end of the housing is fixedly attached to the tip electrode and the proximal end of the housing is fixedly attached to the tubing of the tip section. An electromagnetic sensor cable is connected to the proximal end of the electromagnetic sensor and extends through a lumen in the tip section, through a lumen in the catheter body and into the control handle. The sensor cable is then connected to a circuit board, which is connected to a suitable imaging system.

The control handle is located proximal the catheter body. The control handle comprises a first member fixedly attached to the proximal end of the catheter body and a second member that is movable relative to the first member. A puller wire having proximal and distal ends extends from the control handle, through the catheter body and into the a lumen in the tip section. The distal end of the puller wire is fixedly secured within the tip section, preferably in a blind hole in the tip electrode, and the proximal end of the puller wire is fixedly secured to the second member of the control handle. Manipulation of the first member of the control handle relative to the second member of the control handle moves the puller wire relative to the catheter body, resulting in deflection of the tip section. A compression coil extends through the catheter body in surrounding relation to the puller wire.

A temperature sensor for monitoring the temperature of the tip electrode is also provided. A preferred temperature sensor is a thermocouple comprising a double-stranded enameled wire pair comprising a copper wire and a constant wire. The temperature sensor is anchored within a blind hole in the tip electrode.

DESCRIPTION OF THE DRAWINGS

These and other features and advantages of the present invention will be better understood by reference to the following detailed description when considered in conjunction with the accompanying drawings wherein:

FIG. 1 is a side cross-sectional view of an embodiment of the catheter of the invention.

FIG. 2 is a side cross-sectional view of the catheter body, including the junction between the catheter body and the tip section.

FIG. 3A is a side cross-sectional view of the catheter tip section.

FIG. 3B is an enlarged view of the thermocouple anchored within the tip electrode illustrated in FIG. 3A.

DETAILED DESCRIPTION

Figure 4:
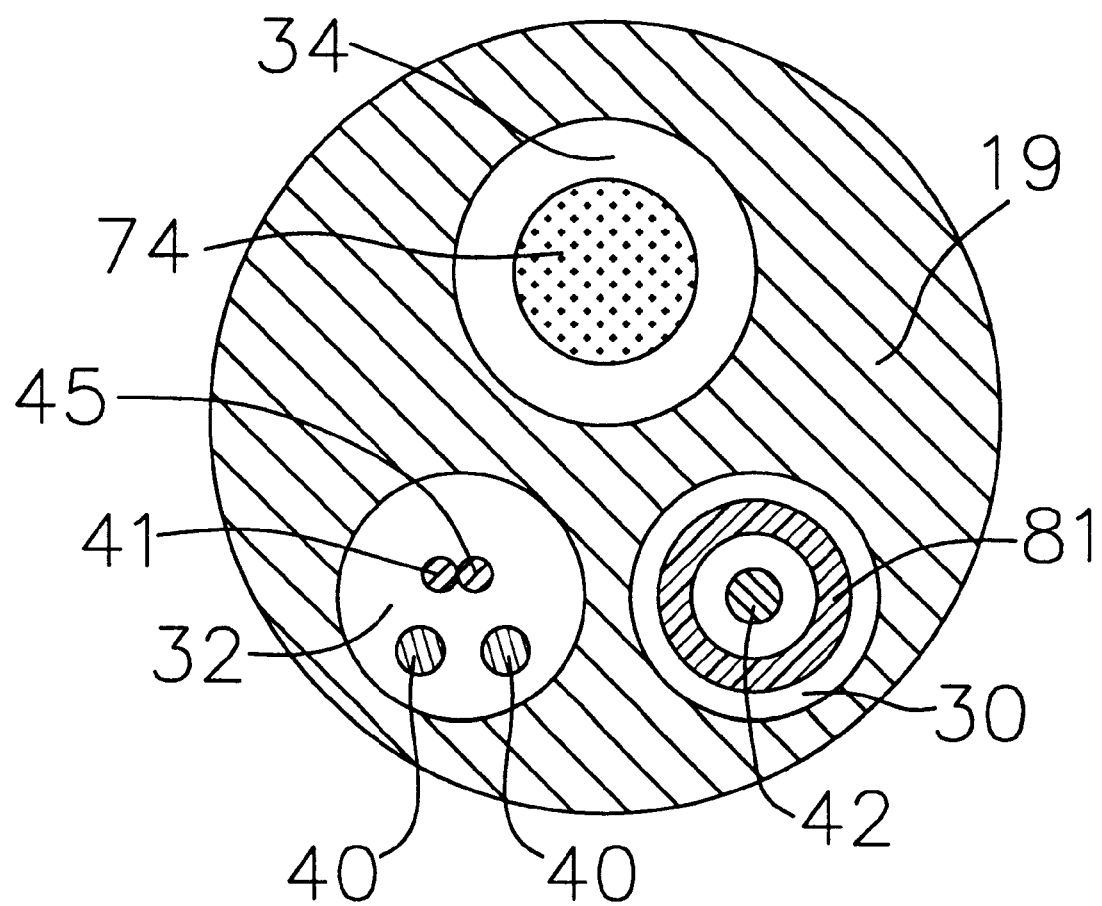
FIG. 4 is a transverse cross-sectional view of the catheter tip section along line 4—4.
Figure 5:
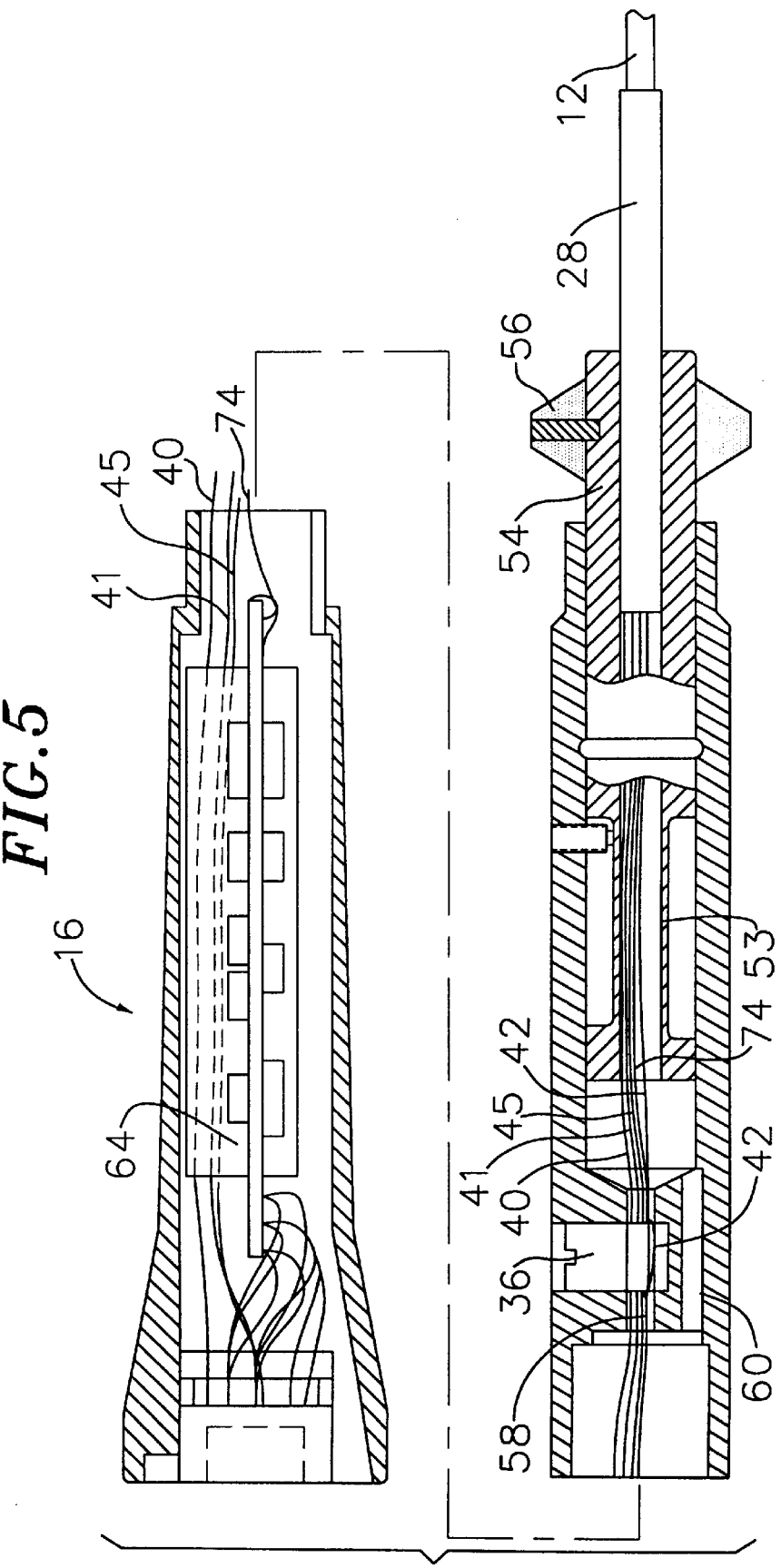
FIG. 5 is a side cross-sectional view of the catheter handle.

In a particularly preferred embodiment of the invention, there is provided a steerable catheter having an electromagnetic sensor. As shown in FIGS. 1–4, the catheter 10 comprises an elongated catheter body 12 having proximal and distal ends, a tip section 14 at the distal end of the catheter body 12, and a control handle 16 at the proximal end of the catheter body 12.

With reference to FIG. 2, the catheter body 12 comprises an elongated tubular construction having a single, axial or central lumen 18. The catheter body 12 is flexible, i.e., bendable, but substantially non-compressible along its length. The catheter body 12 can be of any suitable construction and made of any suitable material. A presently preferred construction comprises an outer wall 22 made of a polyurethane or nylon. The outer wall 22 comprises an imbedded braided mesh of stainless steel or the like to increase torsional stiffness of the catheter body 12 so that, when the control handle 16 is rotated, the tip sectionally of the catheter 10 will rotate in a corresponding manner.

The outer diameter of the catheter body 12 is not critical, but is preferably no more than about 8 french, more preferably no greater than about 7 french. Likewise the thickness of the outer wall 22 is not critical. The inner surface of the outer wall 22 is lined with a stiffening tube 20, which can be made of any suitable material that is less flexible than the outer wall 22, preferably polyimide. The stiffening tube 20, along with the braided outer wall 22, provides improved torsional stability while at the same time minimizing the wall thickness of the catheter, thus maximizing the diameter of the central lumen 18. The outer diameter of the stiffening tube 20 is about the same as or slightly smaller than the inner diameter of the outer wall 22. Polyimide tubing is presently preferred because it may be very thin-walled while still providing very good stiffness. This maximizes the diameter of the central lumen 18 without sacrificing strength and stiffness.

A particularly preferred catheter has an outer wall 22 with an outer diameter of from about 0.090 inch to about 0.094 inch and an inner diameter of from about 0.061 inch to about 0.65 inch and a polyimide stiffening tube 20 having an outer diameter of from about 0.0595 inch to about 0.635 inch and an inner diameter of about from about 0.049 inch to about 0.055 inch.

As shown in FIGS. 3A, 3B and 4, the tip section 14 comprises a short section of tubing 19 having three lumens. The tubing 19 is made of a suitable non-toxic material that is preferably more flexible than the catheter body 12. A presently preferred material for the tubing 19 is braided polyurethane, i.e., polyurethane with an embedded mesh of braided stainless steel or the like. The outer diameter of the tip section 14, like that of the catheter body 12, is preferably no greater than about 8 french, more preferably no greater than about 7 french. The size of the lumens is not critical. In a particularly preferred embodiment, the tip section 14, has an outer diameter of about 7 french (0.092 inch) and the first lumen 30 and second lumen 32 are generally about the same size, having a diameter of about 0.022 inch, with the third lumen 34 having a slightly, larger diameter of about 0.036 inch.

At the distal end of the tip section 14 is a tip electrode 36. Preferably the tip electrode 36 has a diameter about the same as the outer diameter of the tubing 19. A preferred tip electrode 36 has a length of about 6 mm, with an exposed section 37 having a length of about 4 mm and a stem 39, having a diameter less than the diameter of the exposed section 37 and having a length of about 2 mm. The stem 39 and exposed section 37 of the tip electrode 36 are generally solid, having 3 blind holes extending from the proximal end of the stem 39 part way into the exposed section 37.

The tip electrode 36 is connected to the tubing 19 by means of a generally rigid tubular plastic housing 21, preferably made of polyetheretherketone (PEEK). The stem 39 of the tip electrode 36 fits inside the distal end of the plastic housing 21 and is bonded to the housing 21 by polyurethane glue or the like. The proximal end of the plastic housing 21 is bonded with polyurethane glue or the like to the distal end of the tubing 19 of the tip section 14. It is understood that the tip electrode may be connected directly to the tubing 19 of the catheter tip section 14 as desired as is well known in the art.

In the embodiment shown, a ring electrode 38 is mounted on the distal end of the plastic housing 21. The ring electrode 38 is slid over the plastic housing 21 and fixed in place by glue or the like. If desired, additional ring electrodes may be used and can be positioned over the plastic housing 21 or over the flexible tubing 19 of the tip section 14.

A temperature sensing means is provided for the tip electrode 36 and, if desired, the ring electrode 38. Any conventional temperature sensing means, e.g., a thermocouple or thermistor, may be used. A preferred temperature sensing means for the tip electrode 36 comprises a thermocouple formed by an enameled wire pair. One wire of the wire pair is a copper wire 41, e.g., a number 40 copper wire. The other wire of the wire pair is a constant wire 45.The wires 41 and 45 of the wire pair are electrically isolated from each other except at their distal ends where they are twisted together, covered with a short piece of plastic tubing 53, e.g., polyamide, and covered with epoxy. The plastic tubing 53 is then attached in the second blind hole 33 of the tip electrode 36, by polyurethane glue or the like. Alternatively, the wires 41 and 45 can be soldered into the second blind hole 33.

The wires 41 and 45 extend through the second lumen 31 in the tip section 14 and through the central lumen 18 of the catheter body 12. The wires 41 and 45 then extend out through the control handle 16 and to a connector (not shown) connectable to a temperature monitor (not shown).

The tip electrode 36 and ring electrode 38 are each connected to a separate lead wire 40. The lead wires 40 extend through the second lumen 32 of tip section 14, the catheter body 12, and the control handle 16, and each terminate at its proximal end in an input jack (not shown) that may be plugged into an appropriate monitor (not shown). If desired, the portion of the lead wires 40 extending through the catheter body 12, control handle 16 and proximal end of the tip section 14 may be enclosed or bundled within a protective tube or sheath.

The lead wire 40 for the tip electrode 36 is anchored in the first blind hole 31 of the tip electrode by solder or the like. Any other means for anchoring the lead wire in the tip electrode may also be used. Alternatively, the copper wire 41 of the thermocouple can be used as a lead wire for the tip electrode 36.

A lead wire 40 is attached to the ring electrode 38 by any conventional technique. Connection of a lead wire 40 to the ring electrode 38 is preferably accomplished by first making a small hole through the plastic housing 21. Such a hole can be created, for example, by inserting a needle through the plastic housing 21 and heating the needle sufficiently to form a permanent hole. A lead wire 40 is then drawn through the hole by using a microhook or the like. The ends of the lead wire 40 are then stripped of any coating and soldered or welded to the underside of the ring electrode 38, which is then slid into position over the hole and fixed in place with polyurethane glue or the like.

A preferred means for attaching the catheter body 12 to the tip section 14 is illustrated in FIG. 2. The proximal end of the tip section 14 comprises an outer circumferential notch 24 that receives the inner surface of the outer wall 22 of the catheter body 12. The tip section 14 and catheter body 12 are attached by glue or the like. In the arrangement shown, a spacer 52 lies within the catheter body 12 between the distal end of the stiffening tube 20 and the proximal end of the tip section 14. The spacer 52 is preferably made of a material that is stiffer than the material of the tip section 14, e.g., polyurethane, but not as stiff as the material of the stiffening tube 20, e.g., polyimide. A spacer 52 made of Teflon® is presently preferred. A preferred spacer 52 has a length of from about 0.25 inch to about 0.75 inch, more preferably about 0.5 inch. Preferably the spacer 52 has an outer and inner diameter about the same as the outer and inner diameters of the stiffening tube 20. The spacer 52 provides a transition in flexibility at the junction of the catheter body 12 and catheter tip 14, allowing the junction of the catheter body 12 and tip section 14 to bend smoothly without folding or kinking.

The spacer 52 is held in place by the stiffening tube 20. The stiffening tube 20, in turn, is held in place relative to the outer wall 22 by glue joints 23 and 25 at the proximal end of the catheter body 12. In a preferred construction of the catheter body 12, a force is applied to the proximal end of the stiffening tube 20, causing the distal end of the stiffening tube 20 to firmly butt up against and compress the spacer 52. While under compression, a first glue joint 23 is made between the stiffening tube 20 and the outer wall 22 by a fast drying glue, e.g. Super Glue®. Thereafter a second glue joint 25 is formed between the proximal ends of the stiffening tube 20 and outer wall 22 using a slower drying but stronger glue, e.g., polyurethane. Construction of the catheter body 12 whereby the stiffening tube 20 and spacer 52 are under compression has been found to be advantageous to prevent the formation of gaps between the stiffening tube 20 and spacer 52 or between the spacer 52 and the tip section 14 that might otherwise occur after repeated tip deflections. Such gaps are undesirable because they cause the catheter to crease or fold over, hindering the catheter's ability to roll.

A puller wire 42 is provided within the catheter for deflecting the tip section 14. The puller wire 42 is anchored at its proximal end to the control handle 16 and anchored at its distal end to the tip section 14. The puller wire 42 is made of any suitable metal, such as stainless steel or Nitinol, and is preferably coated with Teflon® or the like. The coating imparts lubricity to the puller wire 42. The puller wire 42 preferably has a diameter ranging from about 0.006 to about 0.010 inches.

A compression coil 44 is situated with the catheter body 12 in surrounding relation to the puller wire 42. The compression coil extends from the proximal end of the catheter body 12 to the proximal end of the tip section 14. The compression coil 44 is made of any suitable metal, preferably stainless steel. The compression coil 44 is tightly wound on itself to provide flexibility, i.e., bending, but to resist compression. The inner diameter of the compression coil 44 is preferably slightly larger than the diameter of the puller wire 42. For example, when the puller wire 42 has a diameter of about 0.007 inches, the compression coil 44 preferably has an inner diameter of about 0.008 inches. The Teflon® coating on the puller wire 42 allows it to slide freely within the compression coil 44. Along its length, the outer surface of the compression coil 44 is covered by a flexible, non-conductive sheath 26 to prevent contact between the compression coil 44 and the lead wires 40 within the catheter body 12. A non-conductive sheath 26 made of polyimide tubing is presently preferred.

The compression coil 44 is anchored at its proximal end to the proximal end of the stiffening tube 20 in the catheter body 12 by glue joint 50 and at its distal end to the tip section 14 at a location distal to the spacer 52 by glue joint 51. Both glue joints 50 and 51 preferably comprise polyurethane glue or the like. The glue may be applied by means of a syringe or the like through a hole made between the outer surface of the catheter body 12 and the single lumen 18. Such a hole may be formed, for example, by a needle or the like that punctures the wall of the catheter body 12 and the stiffening tube 20 which is heated sufficiently to form a permanent hole. The glue is then introduced through the hole to the outer surface of the compression coil 44 and wicks around the outer circumference to form a glue joint about the entire circumference of the compression coil 44.

The puller wire 42 extends into the first lumen 30 of the tip section 14. The puller wire 42 is anchored in the first blind hole 31 of the tip electrode 36. Preferably, a ferrule 43, made of stainless steel or the like, is crimped onto the distal end of the puller wire 42 to add thickness to the puller wire. The ferrule 43 is the attached to the inside of the first blind hole 31 of the tip electrode 36 with solder or the like. Alternatively, the puller wire 42 can be anchored to the side of the tip section 14.

With reference to FIGS. 2 and 3, within the tip section 14, and distal to the glue joint 51, the turns of the compression coil are expanded longitudinally. Such expanded turns 47 are both bendable and compressible and preferably extend for a length of about 0.5 inch. The puller wire 42 extends through the expanded turns 47 then into a plastic, preferably Teflon®, sheath 81, which prevents the puller wire 42 from cutting into the wall of the tip section 14 when the tip section 14 is deflected.

An electromagnetic sensor 72 is contained within the distal end of the tip section 14. The electromagnetic sensor 72 is located within the plastic housing 21. The distal end of the electromagnetic sensor 72 extends into the third blind hole 35 in the tip electrode 36 and its proximal end extends into the tubing 19 of the tip section 14. The electromagnetic sensor is fixed in the third blind hole 35 by polyurethane glue or the like. If desired, the third blind hole 35 in the tip electrode 36 may be deeper so that the entire electromagnetic sensor 72 is located within the third blind hole 35. Alternatively, the electromagnetic sensor 72 may be mounted proximal to the tip electrode 36. In another alternative embodiment, the tip electrode 36 has a hollow stem 39 and the electromagnetic sensor 72 is mounted, at least partially, within the hollow stem.

The electromagnetic sensor 72 is connected to an electromagnetic sensor cable 74, which extends through the third lumen 34 of the tip section 14 through the catheter body 12 and out through control handle 16. The electromagnetic sensor cable 74 comprises multiple wires encased within a plastic covered sheath. In the control handle 16, the sensor cable 74 is connected to a circuit board 64. The circuit board 64 amplifies the signal received from the electromagnetic sensor 72 and transmits it to a computer in a form understandable by the computer. Because the catheter is designed for single use only, the circuit board may contain an EPROM chip which shuts down the circuit board approximately 24 hours after the catheter has been used. This prevents the catheter, or at least the electromagnetic sensor, from being used twice.

Suitable electromagnetic sensors for use with the present invention are described, for example, in U.S. Pat. Nos. 5,558,091, 5,443,489, 5,480,422, 5,546,951, 5,568,809, and 5,391,199 and International Publication No. WO 95/02995, the disclosures of which are incorporated herein by reference. A preferred electromagnetic mapping sensor 72 has a length of from about 6 mm to about 7 mm and a diameter of about 1.3 mm.

To use the electromagnetic sensor 72, the patient is placed in a magnetic field generated, for example, by placing a pad containing coils for generating a magnetic field under the patient. A reference electromagnetic sensor is fixed relative to the patient, e.g., taped to the patient's back, and the catheter containing a second electromagnetic sensor is advanced into the patient's heart. Each sensor comprises three small coils which in the magnetic field generate weak electrical signals indicative of their position in the magnetic field. Signals generated by both the fixed reference sensor and the second sensor in the heart are amplified and transmitted to a computer which analyzes the signals and then displays the signals on a monitor. By this method, the precise location of the sensor in the catheter relative to the reference sensor can be ascertained and visually displayed.

Using this technology, the physician can visually map a heart chamber. This mapping is done by advancing the catheter tip into a heart chamber until contact is made with the heart wall. This position and electrograms are recorded and saved. The catheter tip is then moved to another position in contact with the heart wall and again the position is recorded and saved. This procedure is repeated until a three dimensional map of the heart chamber is achieved.

The electromagnetic mapping sensor 72 preferably is used in combination with the tip electrode 36 and ring electrode 38. By combining the electromagnetic sensor 72 and electrodes 36 and 38, a physician can simultaneously map the contours or shape of the heart chamber and the electrical activity of the heart.

The electrode lead wire 40, thermocouple wires 41 and 45, and electromagnetic sensor cable 74 must be allowed some longitudinal movement within the catheter body 12 so that they do not break when the tip section 14 is deflected. To provide for such lengthwise movement, tunnels are provided through the glue joint 50, which fixes the proximal end of the compression coil 44 inside the catheter body 12. The tunnels are formed by transfer tubes 27, preferably made of short segments of polyimide tubing. The transfer tube 27 are each approximately 60 mm long and have outer diameters of about 0.021 inch and inner diameters of about 0.019 inch. The thermocouple wires 41 and 45 and electrode lead wire 40 extend through one transfer tube 27 and the sensor cable 74 extends through a second transfer tube 27. An additional transfer tube 29 is provided at the distal end of the catheter body 12 for the thermocouples wires 41 and 45 and electrode lead wire 40 to pass through glue joint 51.

Longitudinal movement of the puller wire 42 relative to the catheter body 12, which results in deflection of the tip section 12, is accomplished by a suitable manipulation of the control handle 16. The distal end of the control handle 16 comprises a piston 54 with a thumb control 56 for manipulating the puller wire 42. The proximal end of the catheter body 12 is connected to the piston 54 by means of a shrink sleeve 28.

The puller wire 42, lead wires 40 and electromagnetic sensor cable 74 extend through the piston 54. The puller wire 42 is anchored to an anchor pin 36, located proximal to the piston 54. The lead wires 40 and electromagnetic sensor cable 74 extend though a first tunnel 58, located near the side of the control handle 16. The electromagnetic sensor cable 74 connects to a circuit board 64 in the proximal end of the control handle 16. Wires a compute and imaging monitor (not shown).

In another preferred embodiment constructed in accordance with the present invention, two or more puller wires are provided to enhance the ability to manipulate the tip section. In such an embodiment, a second puller wire and a surrounding second compression coil extend through the catheter body and into separate off-axis lumens in the tip section. The lumens of the tip section receiving the puller wires may be in adjacent quadrants. The first puller wire is preferably anchored proximal to the anchor location of the second puller wire. The second puller wire may be anchored to the tip electrode or may be anchored to the wall of the tip section adjacent the distal end of tip section.

The distance between the distal end of the compression coils and the anchor sites of each puller wire in the tip section determines the curvature of the tip section 14 in the direction of the puller wires. For example, an arrangement wherein the two puller wires are anchored at different distances from the distal ends of the compression coils allows a long reach curve in a first plane and a short reach curve in a plane 90° from the first, i.e., a first curve in one plane generally along the axis of the tip section before it is deflected and a second curve distal to the first curve in a plane transverse, and preferably normal to the first plane. The high torque characteristic of the catheter tip section 12 reduces the tendency for the deflection in one direction to deform the deflection in the other direction.

As an alternative to the above described embodiment, the puller wires may extend into diametrically opposed off-axis lumens in the tip section. In such an embodiment, each of the puller wires may be anchored at the same location along the length of the tip section, in which case the curvatures of the tip section in opposing directions are the same and the tip section can be made to deflect in either direction without rotation of the catheter body.

A particularly preferred catheter construction comprising multiple puller wires including control handle construction is disclosed in U.S. patent application Ser. No. 08/924,611 entitled Omni-Directional Steerable Catheter, the disclosure of which is incorporated herein by reference. Such application describes a suitable control handle for manipulating two or more puller wires. The described control handle includes a central passage that may be expanded to accommodate the electrode lead wires, electromagnetic sensor cable, optic fiber and even infusion tube. Further, an extension of the handle may be provided to house the circuit bound for the electromagnetic sensor, e.g., in the same manner as shown in FIG. 4 herein.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention.

Accordingly, the foregoing description should not be read as pertaining only to the precise structures described and illustrated in the accompanying drawings, but rather should be read consistent with and as support to the following claims which are to have their fullest and fair scope.

I claim:

1. A steerable catheter comprising:
   a catheter body having proximal and distal ends and at least one lumen extending therethrough;
   a control handle fixedly attached to the proximal end of the catheter body;
   a tip section comprising:
      a flexible tubing having proximal and distal ends and at least one lumen extending therethrough, wherein the proximal end of the tip section is fixedly attached to the distal end of the catheter body;
      a tip electrode having a distal end and a proximal end mounted at the distal end of the flexible tubing, wherein the tip electrode has a blind hole extending from its proximal end into the electrode to a position proximal its distal end, said blind hole in communication with at least one lumen in the tip section; and
      an electromagnetic sensor having proximal and distal ends, wherein the distal end of the sensor is mounted at least partially within the blind hole in the tip electrode;
   means for connecting the electromagnetic sensor to an imaging system; and
   means for deflecting the tip section.

2. A catheter according to claim 1, wherein the means for connecting the electromagnetic sensor to an imaging system comprises an electromagnetic sensor cable connected to the electromagnetic sensor, wherein the sensor cable extends through a lumen in the tip section, through a lumen in the catheter body and into the control handle.

3. A catheter according to claim 1, wherein the tip section further comprises a generally rigid tubular housing mounted between the distal end of the tip section and the proximal end of the tip electrode, whereby at least part of the electromagnetic sensor is housed within the generally rigid tubular housing.

4. A catheter according to claim 3, wherein the housing is made of polyetheretherketone.

5. A catheter according to claim 3, wherein the tip section further comprises at least one ring electrode mounted on the generally tubular rigid housing.

6. A catheter according to claim 1, wherein the catheter body has a single lumen.

7. A catheter according to claim 6, wherein the catheter body comprises a flexible outer wall and a stiffening tube within the outer wall, wherein the stiffening tube is less flexible than the outer wall.

8. A catheter according to claim 1, wherein the tip section has three lumens.

9. A catheter according to claim 1, wherein the diameter of the tip section is no more than about 7 French.

10. A catheter according to claim 1, wherein the control handle comprises a first member fixedly attached to the proximal end of the catheter body and a second member that is movable relative to the first member.

11. A catheter according to claim 10, wherein the deflecting means comprises a puller wire having a proximal end and a distal end, the puller wire extending from the control handle, through the catheter body and into the a lumen in the tip section, wherein the distal end of the puller wire is fixedly secured within the tip section and the proximal end of the puller wire is fixedly secured to the second member of the control handle, whereby manipulation of the first member of the control handle relative to the second member of the control handle moves the puller wire relative to the catheter body, resulting in deflection of the tip section.

12. A catheter according to claim 11, wherein the distal end of the puller wire is anchored in a blind hole in the tip electrode.

13. A catheter according to claim 11 wherein the deflecting means further comprises a compression coil extending through the catheter body in surrounding relation to the puller wire.

14. A catheter according to claim 1, further comprising a temperature sensor for monitoring the temperature of the tip electrode.

15. A catheter according to claim 14, wherein the temperature sensor is a thermocouple comprising a wire pair comprising a copper wire and a constant on wire.

16. A catheter according to claim 14, wherein the temperature sensor is anchored within a blind hole in the tip electrode.

17. A catheter according to claim 1, wherein the tip section further comprises at least one ring electrode mounted thereon.

18. A catheter according to claim 1, wherein the tip electrode comprises an exposed section at its distal end and a stem at its proximal end.

19. A catheter according to claim 18, wherein the blind hole extends from the proximal end of the stem part way into the interior of the exposed section.

20. A catheter according to claim 18, wherein the stem has a diameter less than the diameter of the proximal end of the exposed section.

21. A steerable electromagnetic catheter comprising:
   a catheter body having proximal and distal ends and at least one lumen extending therethrough;
   a control handle fixedly attached to the proximal end of the catheter body;
   a tip section comprising:
      a section of flexible tubing having proximal and distal ends and a lumen extending therethrough, wherein the proximal end of the tip section is fixedly attached to the distal end of the catheter body;
      a tip electrode having a distal end and a proximal end mounted at the distal end of the flexible tubing, wherein the tip electrode has at least one blind hole extending from the proximal end of the electrode and into the electrode to a position proximal the distal end of the electrode, said blind hole in communication with a lumen in the tip section;
      an electromagnetic sensor having proximal and distal ends, wherein the distal end of the sensor is mounted at least partially within a blind hole in the tip electrode; and
      a generally rigid tubular housing mounted between the distal end of the tubing and the proximal end of the tip electrode, whereby at least part of the electromagnetic sensor is housed within the generally tubular housing; and
   a means for deflecting the tip section.

22. A catheter according to claim 21, wherein the tip electrode comprises an exposed section at its distal end and a stem at its proximal end, wherein the stem is capable of fitting within the distal end of the tubular housing.

23. A catheter according to claim 22, wherein the blind hole extends from the proximal end of the stem part way into the interior of the exposed section.

24. A catheter according to claim 22, wherein the stem has a diameter less than the diameter of the proximal end of the exposed section.

25. A steerable catheter comprising:

a catheter body having proximal and distal ends and at least one lumen extending therethrough;

a control handle fixedly attached to the proximal end of the catheter body, the control handle comprising a first member fixedly attached to the proximal end of the catheter body and a second member that is movable relative to the first member;

a tip section comprising:
   a flexible tubing having proximal and distal ends and at least two lumens extending therethrough, wherein the proximal end of the tip section is fixedly attached to the distal end of the catheter body;
   a tip electrode having a distal end and a proximal end mounted at the distal end of the flexible tubing, wherein the tip electrode has at least two blind holes each extending from the proximal end of the electrode and into the electrode to a position proximal the distal end of the electrode, said blind holes each in communication with a lumen in the tip section; and
   an electromagnetic sensor having proximal and distal ends, wherein the distal end of the sensor is mounted at least partially within one of the at least two blind holes in the tip electrode; and a puller wire having a proximal end and a distal end, the puller wire extending from the control handle, through the catheter body and into the off axis lumen in the tip section, wherein the distal end of the puller wire is fixedly secured within one of the at least two blind holes in the tip electrode and the proximal end of the puller wire is fixedly secured to the second member of the control handle, whereby manipulation of the first member of the control handle relative to the second member of the control handle moves the puller wire relative to the catheter body, resulting in deflection of the tip section.

26. A catheter according to claim 25, wherein the tip electrode comprises an exposed section at its distal end and a stem at its proximal end.

27. A catheter according to claim 26, wherein at least one of the blind holes extends from the proximal end of the stem part way into the interior of the exposed section.

28. A catheter according to claim 26, wherein the stem has a diameter less than the diameter of the proximal end of the exposed section.

29. A steerable catheter comprising:

a catheter body having proximal and distal ends and at least one lumen extending therethrough;

a control handle fixedly attached to the proximal end of the catheter body;

a tip section comprising:
   a section of flexible tubing having proximal and distal ends and a lumen extending therethrough, wherein the proximal end of the tip section is fixedly attached to the distal end of the catheter body;
   a tip electrode having a distal end and a proximal end mounted at the distal end of the flexible tubing, wherein the tip electrode has an exposed section at its distal end and a hollow stem at its proximal end; and
   an electromagnetic sensor having proximal and distal ends, wherein the distal end of the sensor is mounted at least partially within the stem of the tip electrode; and means for deflecting the tip section.

30. A catheter according to claim 29, wherein the tip electrode comprises a blind hole extending from the distal end of the hollow stem part way into the interior of the exposed section.

31. A catheter according to claim 29, wherein the stem has a diameter less than the diameter of the proximal end of the exposed section.

* * * * *